(12) United States Patent
Nuffer et al.

(10) Patent No.: US 8,118,878 B2
(45) Date of Patent: Feb. 21, 2012

(54) ORTHOPEDIC APPLIANCE

(75) Inventors: Juergen Nuffer, Saulheim (DE); Thilo Bein, Darmstadt (DE); Lueder Mosler, Duderstadt (DE); Siegmar Blumentritt, Boesinghausen (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 0 days.

(21) Appl. No.: 12/302,593

(22) PCT Filed: May 23, 2007

(86) PCT No.: PCT/DE2007/000937
§ 371 (c)(1),
(2), (4) Date: Nov. 26, 2008

(87) PCT Pub. No.: WO2007/137560
PCT Pub. Date: Dec. 6, 2007

(65) Prior Publication Data
US 2009/0182434 A1    Jul. 16, 2009

(30) Foreign Application Priority Data
May 30, 2006    (DE) .......................... 10 2006 025 476

(51) Int. Cl.
*A61F 2/64* (2006.01)
(52) U.S. Cl. .............................. 623/47; 623/24; 310/319
(58) Field of Classification Search .................... 623/24, 623/44, 47; 219/211; 36/137; 310/339
See application file for complete search history.

(56) References Cited

U.S. PATENT DOCUMENTS

| | | |
|---|---|---|
| 5,703,474 A | 12/1997 | Smalser |
| 6,875,241 B2 | 4/2005 | Christesen |
| 2002/0138153 A1 | 9/2002 | Nokiuk |
| 2006/0021261 A1 | 2/2006 | Face |
| 2006/0046910 A1 | 3/2006 | Rastegar et al. |
| 2007/0050044 A1 * | 3/2007 | Haynes et al. .................. 623/24 |

FOREIGN PATENT DOCUMENTS

| | | |
|---|---|---|
| EP | 1023872 | 1/2000 |
| FR | 2745476 | 3/1996 |
| FR | 2745476 A1 * | 9/1997 |
| WO | WO00/78170 | 12/2000 |
| WO | WO 2006/135851 | 12/2006 |

OTHER PUBLICATIONS

Shenck, et al.; Energy Scavenging With Shoe-Mounted Piezoelectrics; IEEE Micro IEEE USA; vol. 21, No. 3; May 2001 pp. 30-42.

* cited by examiner

*Primary Examiner* — Bruce E Snow
(74) *Attorney, Agent, or Firm* — Whitham Curtis Christofferson & Cook, PC

(57) ABSTRACT

The invention relates to an orthopedic appliance which is designed to support the weight of a patient and comprises a power supply device for an electrical consumer. The aim of the invention is to be able to convert the kinetic energy introduced into the appliance into electrical energy. To this end, the power supply device comprises a stack (7) of piezoelectric ceramic elements, and the force of the weight is introduced into the stack (7) by means of a force transmission system.

1 Claim, 3 Drawing Sheets

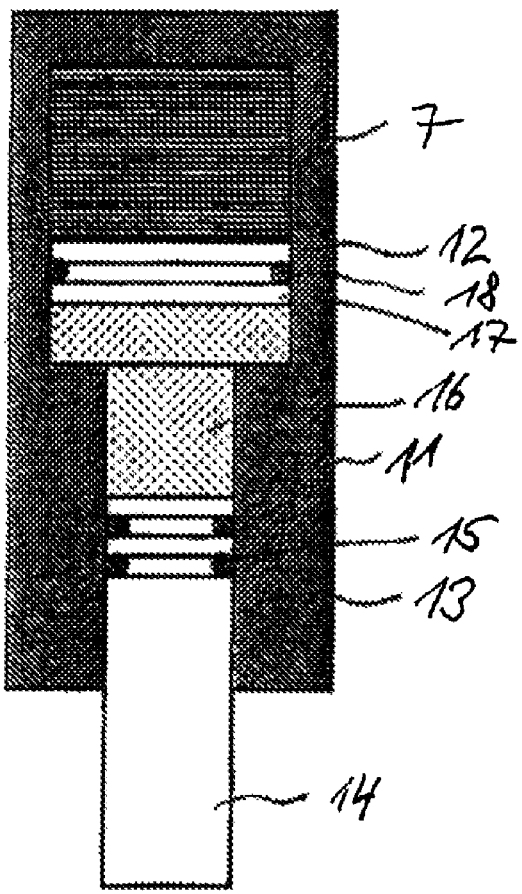
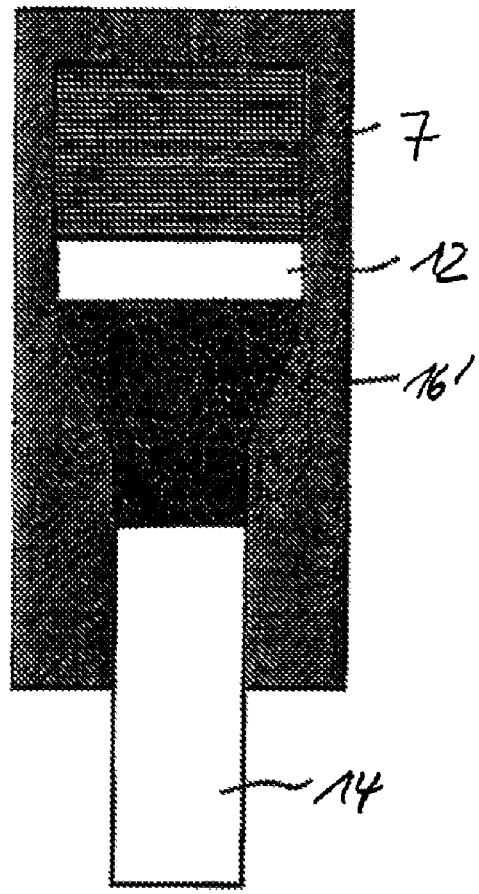
Fig. 3
Fig. 4

ORTHOPEDIC APPLIANCE

The invention relates to an orthopedic appliance which is designed to support the weight of a patient and has a power supply device for an electric consumer.

Orthopedic appliances of the type claimed here are ortheses and in particular prostheses. It is known to fit such appliances with sensors, the electric output signals of which are used to control the properties of the appliance, for example the damping properties of a joint. It is also possible to fit orthopedic appliances of the abovementioned type only with sensors, the sensor signals of which can be transmitted wirelessly to a receiver and as a result enable checking of the suitability of the appliance for the respective prosthesis wearer during functioning.

For supplying sensors and where required actuators or transmission devices it is known to provide a rechargeable battery with electric power, which should as far as possible enable operation of the appliance throughout a single day, in order to be charged at night, that is to say when the appliance is in the unused state. The rechargeable batteries used for this are limited both in their structural size and also in their weight, resulting in a limited charging capacity for the rechargeable battery. It is accordingly problematic to provide additional sensors and if required actuators over and above minimal outfitting.

It is well known, cf. U.S. Pat. No. 5,703,474, to convert a mechanical force into electric power and thus charge a rechargeable battery, for example. It is also known to use the ground reaction force produced by the weight of the person during walking for piezoelectric power extraction. IEEE MICRO, volume May-June 2001, pages 30 to 42 describes a piezoelectric arrangement which is connected to a flexible film in a shoe sole. The extracted power is used to illuminate the shoe sole. The electric power extractable using a piezoelectric element on a flexible film is minimal and thus not suited to application in an orthopedic appliance of the abovementioned type.

The aim of the present invention is to supply an orthopedic appliance, which is if required fitted with several sensors and/or actuators, with adequate power, preferably using a rechargeable battery.

This task is solved by an orthopedic appliance according to the invention of the abovementioned type in that the power supply device has a stack of piezoelectric ceramic elements and that the force of the weight is introduced to the stack via a force transmission arrangement.

According to the invention stacks of rigid piezoceramic elements are therefore used, which however have to be activated by higher forces to extract the required power than are exerted by the normal weight of a person. It is therefore provided according to the invention that the force is introduced to the stack from the piezoelectric ceramic elements by a force transmission arrangement. This makes it possible to multiply the force resulting from the weight and thus make it useful for meaningful use with a piezoceramic stack.

The stack is preferably connected electrically to a rechargeable battery via a converter circuit. This makes it possible for example, when walking with a prosthesis, to utilize the forces of weight absorbed by the latter to extract electric power and thus charge the rechargeable battery. Even if charging the rechargeable battery is incomplete the operating time of the rechargeable battery can be considerably prolonged by the power extraction with the piezoceramic stack. Charging the rechargeable battery overnight must not be replaced by this.

The force transmission arrangement can for example be a turning lever, which is connected via a short lever arm to the stack and via which the force of the weight is introduced with a long lever arm. This successfully produces a translation of force for example by a factor of 5, if the inventive power supply device is built into a foot prosthesis. Power extraction can further be boosted by two stacks with piezoelectric ceramic elements being arranged on both sides of the pivot point of the turning lever, such that both the force during heel strike and the rolling force over the ball of the foot can be used during a walking cycle. With such an arrangement more axial forces can also be successfully used, which arise merely from switching weight from one leg to the other when standing.

It is appropriate in particular for absorbing axial forces if the force transmission device is a pressure transmission arrangement with transferring surfaces of varying size. Such a force transmission arrangement can for example be incorporated very usefully into a modular pipe of a lower-leg prosthesis in order to use the force of the weight transferred via the pipe to the foot prosthesis and thus to the ground for extracting useful electric power.

The invention will be explained in greater detail hereinbelow by way of exemplary embodiments illustrated in the diagram, in which:

FIG. 3 shows an arrangement built into a pipe of a stack of plates with a hydraulic force transmission arrangement;

FIG. 4 shows an arrangement according to FIG. 3, but with a force transmission arrangement formed by an elastomer.

Figure 1:
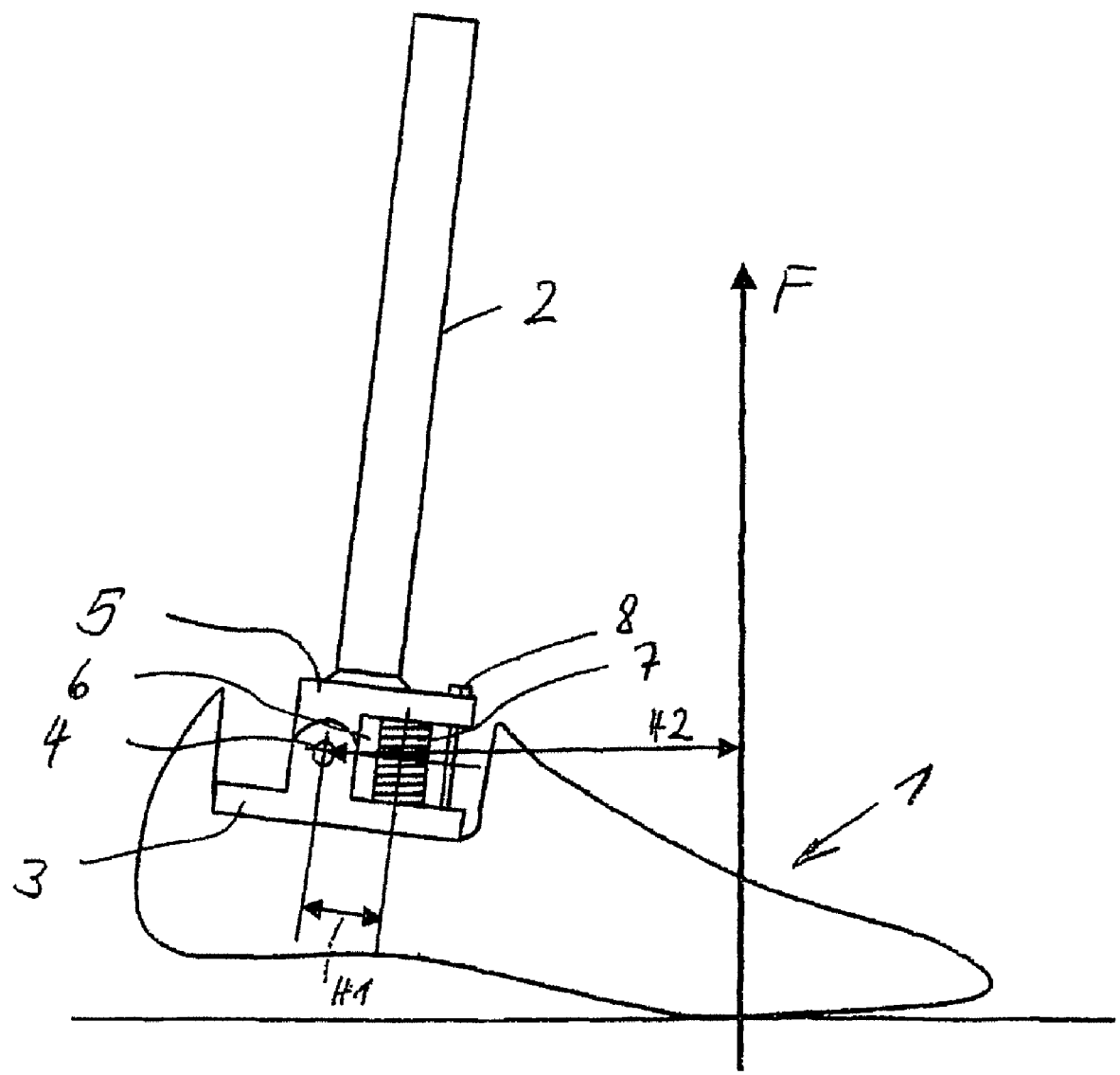
FIG. 1 shows a vertical section through a foot prosthesis with a stack of piezoelectric ceramic elements arranged adjacent to a hinge joint.

FIG. 1 schematically shows a foot prosthesis 1 with a modular pipe 2 connected via an adapter (covered here). The foot prosthesis 1, not illustrated here in greater detail in its inner structure, contains a connecting plate 3 with a hinge joint 4, via which an adapter plate 5 fitted with the adapter is connected rotatably to the connecting plate 3. With the connecting plate 3 the adapter plate 5 forms an interstice 6 which is filled with a stack 7 of piezoelectric ceramic elements. An adjustable screw 8 is guided in through the adapter plate 5 and anchored in the connecting plate 3 so that the screw 8 limits movement of the adapter plate 5 relative to the connecting plate 3 in the direction of opening.

It is evident that the stack 7 is arranged with a short lever arm H1 with respect to the hinge joint 4, while the ground reaction force F acts via the long lever arm H2 on the hinge joint 4 when rolling over the ball of the foot, so that the force acting on the stack 7 is multiplied relative to the ground reaction force F.

Figure 2:
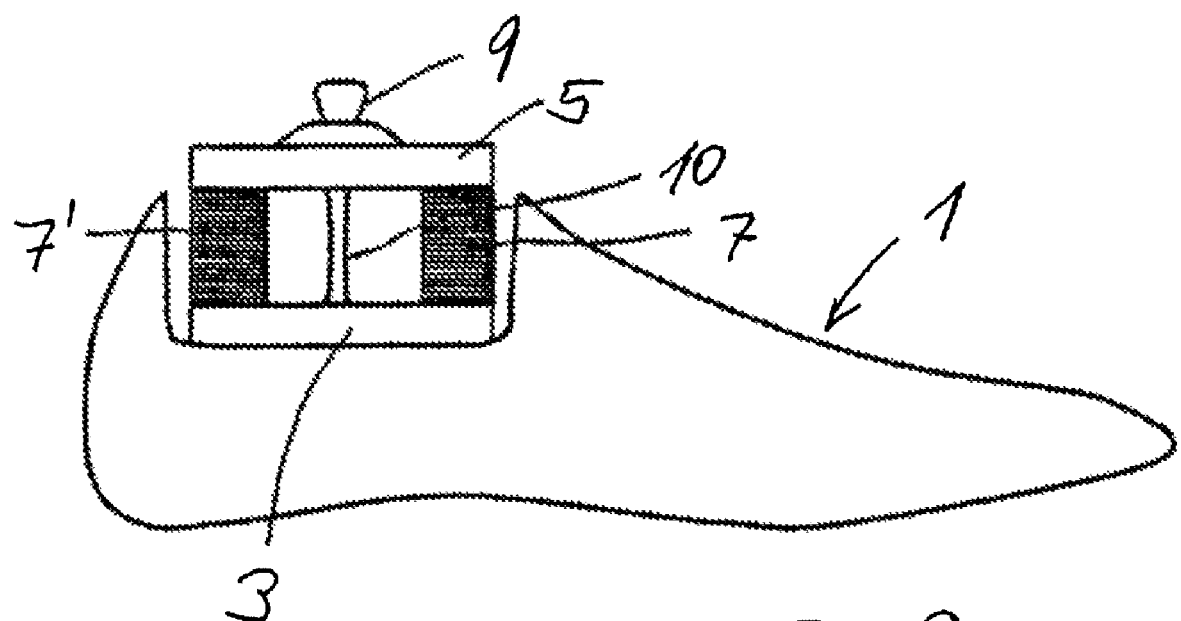
FIG. 2 shows a foot prosthesis according to FIG. 1 with two stacks of plates arranged on both sides of a force introduction axis.

The arrangement illustrated in FIG. 2 shows the adapter 9 which is attached to the adapter plate 5. The adapter plate 5 is connected to the connecting plate 3 via a connecting element 10 designed as a tensile element, next to which in each case there is a stack 7, 7' in the direction of the foot at the front and the rear.

The stack lying at the front in the direction of the foot fulfills the same function as the stack 7 in FIG. 1. The stack 7', arranged at the rear in the direction of the foot, therefore pointing to the heel, serves for the additional absorption of the heel strike forces when the foot strikes the ground during a walking cycle. The two stacks 7, 7' together can additionally absorb axial forces exerted without torque on the foot at the level of the ankle joint, for example when merely switching weight from one leg to the other when standing (here from the healthy leg to the leg fitted with the prosthesis).

Whereas FIGS. 1 and 2 show the stacks 7, 7' and the force transmission arrangement in the ankle region of a foot prosthesis 1, in the exemplary embodiments in FIGS. 3 and 4 the stack 7 with the associated force transmission arrangement is preferably arranged in the modular pipe 2. A cylindrical housing 11 which can be inserted into the modular pipe 2 is provided for this, which housing 11 has a cylindrical chamber 12, with a large diameter and sealed on the front side, and a cylindrical chamber 13, adjacent to the latter and with a smaller diameter. In the cylindrical chamber 13 a piston 14 is guided, which is sealed by two O-rings 15 relative to the cylindrical chamber 13. The piston 14 delimits a hydraulic volume 16, which extends into the larger cylindrical chamber 12 as far as a piston 17, the diameter of which is adapted to the diameter of the cylindrical chamber 12 and which is likewise sealed by an O-ring 18 relative to the chamber 12 so that there is a sealed hydraulic volume 16. The piston 17 is connected to the stack 7 arranged in the chamber 12, which stack 7 is thus supported on the closed front wall of the housing 11. The force of the weight or ground reaction force F introduced via the piston 14 acts on the hydraulic volume 16. The pressure thus resulting in the hydraulic volume 16 is distributed evenly over the volume and acts on the piston 17 having a larger cross-sectional area and resting on the corresponding stack 7. A significantly greater force is exerted thereby on the stack 7. The triggering force of the weight can be translated with such an arrangement for example with a factor of 10.

In the exemplary embodiment illustrated in FIG. 4 the piston 14 acts on an elastomer piece 16' extending from the chamber 13 to the chamber 12, which elastomer piece 16' rests on the piston 12 with a relatively large surface. The elastomer 16' behaves like a hydraulic fluid and provides uniform pressure exerted on all sides, whereby the force translation works on the piston 12. The advantage of the embodiment illustrated in FIG. 4 is that sealing of the hydraulic volume 16 can be omitted and the problem with leakage of hydraulic oil does not have to be addressed.

The illustrated exemplary embodiments thus practicably enable extraction of electric power from the force of the weight introduced to the prosthesis during walking.

The force of the weight introduced to an orthesis can similarly also be used for conversion to electric power to control the support properties of the orthesis.

The invention claimed is:

1. An orthopedic appliance which is designed to support the weight of a patient, comprising:
   at least one stack of piezoelectric ceramic elements configured in a force transmission arrangement between a pair of plates arranged for introducing actual force of weight of the patient into the stack of piezoelectric ceramic elements thereby increasing by multiplying the force resulting from the weight wherein said stack of piezoelectric ceramic elements are offset from a connector which connects said pair of plates and allows movement of said plates relative to one another at said stack of piezoelectric ceramic elements;
   wherein the force transmission arrangement is a turning lever having a short lever arm and a long lever arm which is connected to the stack of piezoelectric ceramic elements, and wherein the force of the weight is introduced with said long lever arm; and
   wherein said at least one stack of piezoelectric ceramic elements includes two stacks with piezoelectric ceramic elements arranged on both sides of a pivot point of the turning lever.

* * * * *